United States Patent [19]

Goorsky et al.

[11] Patent Number: 4,758,298
[45] Date of Patent: Jul. 19, 1988

[54] METHOD FOR FORMING MULTIPLE SENSOR BUNDLE

[75] Inventors: Mark S. Goorsky, Niles; Mark B. Koch, Mt. Prospect; Richard C. Murray, Jr., Palatine, all of Ill.

[73] Assignee: Spectramed, Inc., Newport Beach, Calif.

[21] Appl. No.: 936,388

[22] Filed: Dec. 1, 1986

Related U.S. Application Data

[62] Division of Ser. No. 779,342, Sep. 23, 1986, Pat. No. 4,706,677.

[51] Int. Cl.$^4$ .................. B29D 11/00; B05D 5/06
[52] U.S. Cl. .................... 156/296; 264/1.5; 427/163
[58] Field of Search ............ 156/166, 180, 296, 391, 156/244.12, 244.22; 264/1.5, 261, 263, 264; 128/633, 634, 642, 664–667; 356/39; 350/96.24, 96.29, 96.30; 65/3.4, 3.11; 427/163; 118/234

[56] References Cited

U.S. PATENT DOCUMENTS

| | | | |
|---|---|---|---|
| 3,646,186 | 2/1972 | Hager | 264/1.5 X |
| 4,099,837 | 7/1978 | Vazirani | 350/96.29 |
| 4,200,110 | 4/1980 | Peterson et al. | 128/634 |
| 4,264,649 | 4/1981 | Claypoole et al. | 264/1.5 X |
| 4,344,438 | 8/1982 | Schultz | 128/634 |
| 4,560,248 | 12/1985 | Cramp et al. | 128/634 X |

OTHER PUBLICATIONS

Baim et al., "Simultaneous Measurement of Coronary Venous Blood Flow and Oxygen Saturation during Transient Alterations in Myocardial Oxygen Supply and Demand", Amer. J. of Cardiology, vol. 49, Mar. 1982, pp. 743–752.
Volz et al., "A Neonatal Fiberoptic Probe for Oximetry and Dye Curves", IEEE Trans. on Biomed. Eng., vol. BME-26, No. 7, Jul. 1979, pp. 416–422.
Johnston et al., "Body Tissue Transducer", IBM Tech. Disc. Bull., vol. 6, No. 8, 1964, pp. 13–14.
Band et al., J. Physiol., (London), 266, 12, 1977, pp. 57–58.
Personal Communication of D. Markle, 1982.

Primary Examiner—Michael Ball
Assistant Examiner—Geoffrey L. Knable
Attorney, Agent, or Firm—Lyon & Lyon

[57] ABSTRACT

A multiple sensor which can be readily inserted into, and removed from a radial arterial cannula for use in continuous in vivo patent monitoring includes a plurality of individual sensors, each sensor including a sensing element disposed on an optical waveguide, the sensors being bonded together by an adhesive without covering the sensing elements.

9 Claims, 1 Drawing Sheet

U.S. Patent  Jul. 19, 1988  4,758,298
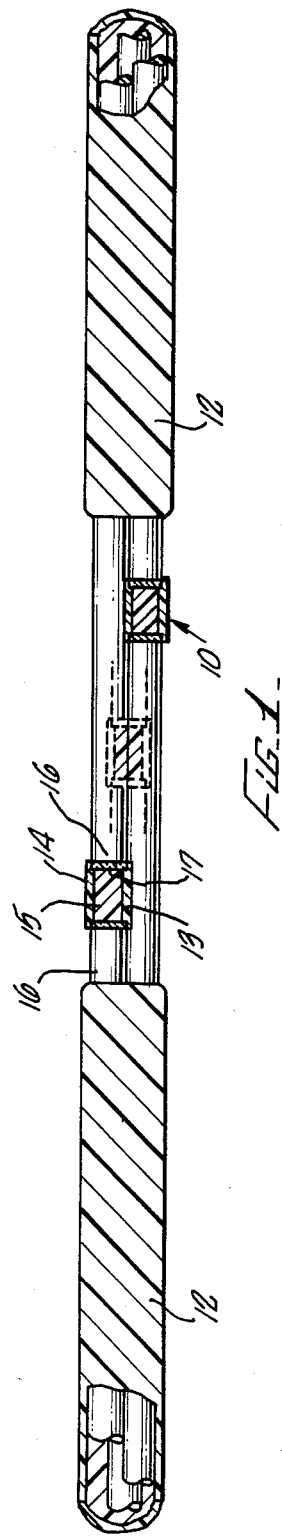
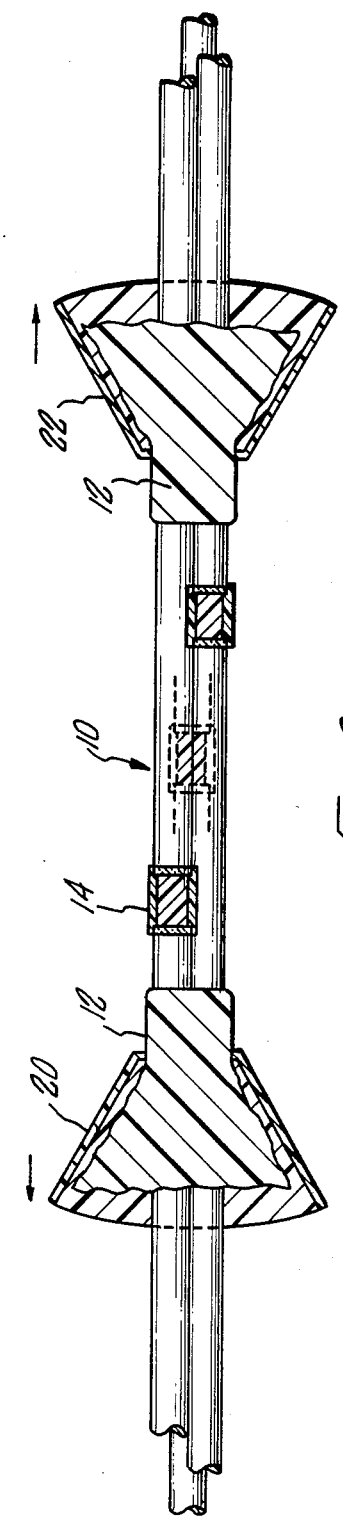

METHOD FOR FORMING MULTIPLE SENSOR BUNDLE

This application is a division of application Ser. No. 779,342, filed Sept. 30, 1986, now U.S. Pat. No. 4,706,677.

BACKGROUND OF THE INVENTION

This invention relates generally to in vivo sensors and more particularly to multiple sensors for use in arterial cannulae. Present in vivo sensors for medical applications are large and require insertion into major arteries. Recently, several miniature sensors using optical waveguides for the transmission of information have been developed for in vivo monitoring. Such miniature sensors have always been mounted in supporting enclosures such as catheter lumens, hypodermic needles, or other small tubes. Examples of miniature sensor systems include the catheter mounted K+ sensors described by D. M. Band and T. Treasure, *J. Physiol.* (London), 266, 12 (1977) and by M. S. Goorsky, J. S. Fowler, and R. C. Murray, Jr. in U.S. patent application Ser. No. 699,369 filed Feb. 7, 1985, now U.S. Pat. No. 4,653,499, and the needle-mounted fiber optic pH sensor described by D. R. Markle et al., A pH Measurement System For Use in Tissue & Blood, NIH, (personnal communication). Such sensor systems, mounted in needles or tubes, are not suited for use in radial arterial cannulae or for applications in other small arteries because they are either too large, too stiff, or cannot accommodate multiple sensors and still remain small and flexible. Radial arterial cannulae typically have a diameter of 900 $\mu$m or less, thus limiting the size of the inserted sensor. Advantages for using radial or other small arteries for in vivo sensor insertion include: easier accessibility, less trauma to the patient, and lower risk of serious side effects or damage to major arteries. Therefore, it is an object of the present invention to provide a multiple sensor bundle which can be readily inserted into, and removed from, a radial or other small artery cannula for use in continuous in vivo patient monitoring.

Additional objects, advantages, and novel features of the invention will be set forth in part in the description which follows and in part will become apparent to those skilled in the art upon examination of the following or may be learned by practice of the invention.

SUMMARY OF THE INVENTION

To achieve the foregoing and other objects and in accordance with the purposes of the present invention, a multiple sensor for insertion into an arterial cannula may comprise: a plurality of sensors, each sensor including a sensing element disposed on an optical waveguide; said sensors being bonded together by an adhesive; wherein said sensing elements are positioned from one another so as to maximize exposure to a sensing environment. A method of forming such a sensor may include the steps of placing a plurality of sensors together to form a bundle, each sensor including a sensing element disposed on an optical waveguide, said sensors being positioned from one another to maximize exposure to a sensing environment; placing a funnel-shaped hollow tube over each end of said bundle; applying an adhesive into each funnel on said bundle without covering said sensing elements; moving each of said funnels over its respective bundle end to uniformly coat said end with said adhesive and to remove said tubes from said bundle; and curing said adhesive.

DESCRIPTION OF THE DRAWINGS

The present invention is illustrated in the following drawings wherein:

FIG. 1 is a schematic illustration of one embodiment of the subject invention wherein the multiple sensor includes three individual sensors.

FIG. 2 is a schematic illustration of a method of making one embodiment of the subject invention.

DETAILED DESCRIPTION OF THE INVENTION

Referring to FIG. 1, three individual sensors 10 are bonded together with adhesive 12, which has been applied so as to leave the individual sensing elements 14 uncovered. Each sensor 10 includes sensing element 14 which is shown positioned between the ends of two pieces of optical fiber 16.

Individual miniature sensors for use in the construction of a multiple sensor include a sensing element disposed on an optical waveguide, preferably a single 250 $\mu$m diameter fiber. Most individual sensors place the sensing element at the distal end of the optical fiber. However, this method of construction is not suitable for use in a multiple sensor bundle because the sensing elements should not be covered with the adhesive and yet the end of the bundle which is inserted into the cannula must be held together to prevent the sensors from splaying apart. To overcome this problem, each individual sensor is constructed with the sensing element between two ends of optical fiber.

One example of individual sensor construction includes placing a hollow-fiber membrane 13 over the ends of two fibers 16. The space between the fiber ends within the membrane is filled with a sensing gel 15 and a mirror 17, placed at the back end of the sensing region. Polyurethane adhesive binds the fibers to the membrane and mirror.

In FIG. 1 each sensor 10 is positioned so as to maximize exposure of the sensing element 14 to the intended environment. Preferably the sensing elements are slightly staggered from one another, as shown in FIG. 1.

Referring to FIG. 2, a multiple sensor is made by placing three sensors 10 in a bundle with the sensing elements 14 next to each other, but slightly staggered. Two optical ferrules 20 and 22 (or other funnel-shaped hollow tubular structures) are placed over each end of the bundle of sensors and slid together so that their front (smaller) ends are facing one another but are away from the sensing elements. Each ferrule is then filled with an adhesive 12 and when each ferrule is pulled off the fiber bundles, a uniform coating of adhesive is applied to the fibers. When the adhesive cures, the fibers are bonded to one another. The excess fiber on the distal end of the multiple sensor can be cut off as required for insertion into the arterial cannula, however a small length of excess optical fiber at the insertion end is required to bond the fibers together without bonding the sensing elements or applying adhesive thereto. Each individual sensor in the bundle can be attached to a separate fiber-optic measuring system.

Choices of adhesive include polyurethane or silicone rubber adhesive for flexible bonding and epoxys such as Tracon FDA yellow (pre-cured for one to two hours) if a more rigid bundle is required.

The multiple sensor can be made of any number of individual sensors. If needed, plain fiber can be substituted for a sensor thereby retaining the structural support. The overall size of the multiple sensor is determined by the number of sensors required and the diameter of each sensor. The multiple sensor bundle will become less flexible as more sensors or fibers are added. Also, the number of individual sensors (and/or plain fibers) will be limited by the diameter of the arterial cannula used. The multiple sensor of the present invention is easily used by direct insertion into an arterial cannula. Multiple sensors can be made which will readily fit a radial arterial cannula.

Advantages of the multiple sensor of the subject invention are many. The sensor bundles have uniform cross-section, a precisely determined diameter (determined by the ferrules used to form them), and do not require an outer support sleeve. The bundles are sturdy, but can be made as flexible or as stiff as required. The adhesive coating material can be chosen for biocompatibility and antithrombogenicity. An example of a biocompatible adhesive is Biothane brand polyurethane. Virtually all of the sensing element surface is exposed to the environment, thereby resulting in faster responses than in sensors enclosed in a sleeve or a hypodermic needle with a cutout.

We claim:

1. A method of forming a multiple sensor device comprising the steps of:
   (a) placing a plurality of sensors, each sensor including a sensing element and optical waveguide pieces longitudinally spaced from each other, said sensing element being disposed in the space between the ends of first and second optical waveguide pieces having ends in spaced relationship, together to form a bundle having a first end and a second end such that said sensing elements are between said first and second bundle ends;
   (b) placing a funnel-shaped hollow tube around said bundle at a point between one end of the bundle and the sensing element longitudinally closest to that end of said bundle by sliding said funnel-shaped hollow tube over said bundle such that the larger diameter end of said funnel-shaped tube faces toward said one end of the bundle;
   (c) placing a second funnel-shaped hollow tube at a point between the other end of said bundle and the sensing element longitudinally closest to that end such that the larger diameter end of said second funnel-shaped hollow tube faces toward said other end of the bundle
   (d) supplying an adhesive into each said funnel-shaped hollow tube on said bundle;
   (e) sliding each said funnel-shaped hollow tube outwardly to uniformly coat that portion of said bundle from each said point to the respective end of the bundle without coating said sensing elements with said adhesive and to remove each said funnel-shaped hollow tube from said bundle; and
   (f) curing said adhesive.

2. The method of claim 1 wherein said bundle is of a size small enough to permit use in a radial arterial cannula.

3. The method of claim 1 wherein said optical waveguides are formed of 250 $\mu$m diameter optical fiber.

4. The method of claim 1 wherein said adhesive is selected from the group consisting of polyurethane, silicone rubber adhesive, and epoxy.

5. The method of claim 1 wherein said adhesive is formed of a material having the properties of biocompatibility and nonthrombogenicity.

6. The method of claim 1 wherein said funnel-shaped hollow tube comprises an optical ferrule.

7. The method of claim 1 wherein each sensing element comprises a sensing gel and a hollow-fiber membrane positioned over the ends of said first and second waveguide pieces and with said sensing gel located in the space therebetween.

8. The method of claim 1 wherein said sensing elements are longitudinally staggered from each other.

9. The method of claim 1 wherein said outwardly sliding step is performed substantially contemporaneously at each end of said bundle.

* * * * *